US011260099B2

United States Patent
Jackson et al.

(10) Patent No.: US 11,260,099 B2
(45) Date of Patent: Mar. 1, 2022

(54) PET FOOD COMPOSITIONS

(71) Applicant: Hill's Pet Nutrition, Inc., Topeka, KS (US)

(72) Inventors: Matthew Jackson, Topeka, KS (US); Dennis Jewell, Lawrence, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 823 days.

(21) Appl. No.: 15/381,835

(22) Filed: Dec. 16, 2016

(65) Prior Publication Data

US 2018/0169173 A1 Jun. 21, 2018

(51) Int. Cl.

| A61K 36/82 | (2006.01) |
|---|---|
| A23K 50/00 | (2016.01) |
| A23K 50/48 | (2016.01) |
| A23K 10/30 | (2016.01) |
| A23K 20/00 | (2016.01) |
| A23K 40/30 | (2016.01) |
| A23K 50/40 | (2016.01) |
| A23K 20/10 | (2016.01) |
| A61K 36/21 | (2006.01) |
| A61K 36/752 | (2006.01) |

(52) U.S. Cl.
CPC .............. *A61K 36/82* (2013.01); *A23K 10/30* (2016.05); *A23K 20/00* (2016.05); *A23K 20/10* (2016.05); *A23K 40/30* (2016.05); *A23K 50/00* (2016.05); *A23K 50/40* (2016.05); *A23K 50/48* (2016.05); *A61K 36/21* (2013.01); *A61K 36/752* (2013.01)

(58) Field of Classification Search
None
See application file for complete search history.

(56) References Cited

U.S. PATENT DOCUMENTS

| 5,053,234 | A | * | 10/1991 | Anderson | A23J 3/341 |
|---|---|---|---|---|---|
| | | | | | 426/59 |
| 6,068,862 | A | | 5/2000 | Ishihara et al. | |
| 6,093,418 | A | * | 7/2000 | Sunvoid | A23K 10/37 |
| | | | | | 424/438 |
| 6,936,598 | B2 | | 8/2005 | Khoo | |
| 8,691,303 | B2 | | 4/2014 | Sunvold et al. | |
| 9,265,276 | B2 | | 2/2016 | Bortlik et al. | |
| 2003/0215547 | A1 | * | 11/2003 | Leyh, Jr. | A23P 20/12 |
| | | | | | 426/98 |
| 2007/0128310 | A1 | * | 6/2007 | Honda | A61K 31/122 |
| | | | | | 426/2 |
| 2008/0085338 | A1 | | 4/2008 | Krammer | |
| 2008/0299286 | A1 | | 12/2008 | Josephson | |
| 2010/0112136 | A1 | | 5/2010 | Ward | |

FOREIGN PATENT DOCUMENTS

| CN | 104982653 A | * | 10/2015 |
|---|---|---|---|
| EP | 0951838 A1 | | 10/1999 |
| EP | 23246357 A1 | | 7/2011 |
| EP | 2346357 | | 6/2016 |
| JP | 03019656 A | * | 1/1991 |
| JP | 2004357505 | | 12/2004 |
| JP | 2005-065750 A | | 3/2005 |
| RU | 2375065 | | 12/2009 |
| RU | 2491009 | | 8/2013 |
| WO | 97/45023 A1 | | 12/1997 |

OTHER PUBLICATIONS

Tea Processing, 2019 https://en.wikipedia.org/wiki/Tea_processing.*
Hayashi, 2013, "Composition for the prevention or improvement or irritable bowel syndrome, comprises Litchi fruit or its extract as an active ingredient," Database WPI Thomson AN: 2013-B51027 & JP 2013-018753A.
International Search Report and Written Opinion of the International Searching Authority in International Application No. PCT/US2017/063822, dated Feb. 12, 2018.
Kanamaru, 1996, "Pet food with good dietary effect—contains unsatd. Fatty acid, dietary fibre and Chinese medicine, e.g., eucommia or ginseng," Database WPI Thomson AN: 1996-395965 & JP H08-191668A.
Matsuoka, 2004, "Supplement for reducing or preventing gastrointestinal disease in dogs, contains beer yeast, live microbial agent, oligosaccharide and tea extract," Database WPI Thomson AN: 2005-043672 & JP 2004-357505A.

* cited by examiner

*Primary Examiner* — Terry A McKelvey
*Assistant Examiner* — Catheryne Chen

(57) ABSTRACT

Described herein are pet food compositions comprising a *Camellia* extract obtained from the tissue of a tea which is greater than about 40% oxidized; and a fiber component, wherein the *Camellia* extract and the fiber component are present in an amount effective to provide, after about 24 hours post-ingestion, a fecal hydrogen sulfide concentration of less than 450 mg/L, and a colonic lumen pH of less than 5.0. Methods of making and using these pet food compositions are also described.

20 Claims, No Drawings

PET FOOD COMPOSITIONS

BACKGROUND

Maintaining a healthy colonic environment is a challenge in companion animals, as their lower intestine is typically of shorter length than herbivores or omnivores; a shorter colon results in reduced potential for production and absorption of microbial metabolites known to improve colon health. Acidification of the colonic lumen by commensal lactic acid bacteria is critical to the process of curating a healthy microbiome; with a relatively short colon length, it is likely that companion animals would benefit from enhancement of commensal microbial fermentation and subsequent colonic acidification. Apart from health benefits of colon acidification via production of lactic acid and SCFA, there are detrimental consequences to microbial production of odiferous hydrogen sulfide, branched short chain fatty acids (BSCFAs) and protein putrefaction products can have negative consequences for health and social interaction (e.g., gas, bowel distension, irritable bowel syndrome, and renal dysfunction).

The development of pet food compositions which are able to improve the colonic environment by diverting the fermentation capacity of gut commensal microbiota toward lactic acid (lactate) production and away from production of molecules which have negative consequences for health and social interaction has been a challenge. In particular, an optimal health solution would encourage ample fermentation by commensal gut bacteria, but not produce clinically significant amounts of gas; it is not straightforward to predict which combinations of dietary ingredients will enhance fermentation to lactate at the expense of gas formation and protein putrefaction. Embodiments of the present invention are designed to meet these needs.

BRIEF SUMMARY

In some embodiments, the present invention provides a pet food composition comprising: a *Camellia Sinensis* (hereafter, *Camellia*) extract obtained from the tissue of a tea which is greater than about 40% oxidized; and a fiber component, wherein the *Camellia* extract and the fiber component are present in an amount effective to provide, after about 24 hours post-ingestion, a fecal hydrogen sulfide concentration of less than 450 mg/L, and a colonic lumen pH of less than 5.0.

Other embodiments provide methods for treating, preventing, or ameliorating a symptom of a gastrointestinal disease, condition or disorder in a companion animal, comprising administering an effective amount of the composition according to any foregoing claim, to a companion animal in need thereof.

Further embodiments provide methods for maintaining the homeostatic balance of the intestinal ecosystem of a companion animal, comprising administering an effective amount of the composition according to claim 1, to a companion animal in need thereof.

DETAILED DESCRIPTION

In some embodiments, the present invention provides a pet food composition comprising: a *Camellia* extract obtained from the tissue of a tea which is greater than about 40% oxidized; and a fiber component. In some embodiments, the *Camellia* extract and the fiber component are present in an amount effective to provide, after about 24 hours post-ingestion, a fecal hydrogen sulfide concentration of less than 450 mg/L. In some embodiments, the *Camellia* extract and the fiber component are present in an amount effective to provide, after about 24 hours post-ingestion, a colonic lumen pH of less than 5.0.

In some embodiments, the *Camellia* extract is obtained from the tissue of a tea which is greater than about 45% oxidized. In some embodiments, the *Camellia* extract is obtained from the tissue of a tea which is greater than about 50% oxidized. In some embodiments, the *Camellia* extract is obtained from the tissue of a tea which is greater than about 55% oxidized. In some embodiments, the *Camellia* extract is obtained from the tissue of a tea which is greater than about 60% oxidized. In some embodiments, the *Camellia* extract is obtained from the tissue of a tea which is greater than about 65% oxidized. In some embodiments, the *Camellia* extract is obtained from the tissue of a tea which is greater than about 70% oxidized. In some embodiments, the *Camellia* extract is obtained from the tissue of a tea which is greater than about 75% oxidized. In some embodiments, the *Camellia* extract is obtained from the tissue of a tea which is greater than about 80% oxidized. In some embodiments, the *Camellia* extract is obtained from the tissue of a tea which is greater than about 85% oxidized. In some embodiments, the *Camellia* extract is obtained from the tissue of a tea which is greater than about 90% oxidized.

In some embodiments, the fiber component comprises a fermentable fiber. In other embodiments, the fiber component comprises a fiber type selected from: a hemicellulose; a cellulose; pectin; an oligosaccharide of xylose, galactose or fructose; a resistant starch, and a combination of two or more thereof.

Further embodiments provide pet food compositions wherein the fiber component comprises a soluble fiber source. In some embodiments, the soluble fiber source is selected from: oats; apple; sugar cane; citrus pulp; beet pulp; grains, or a combination of two or more thereof. In some embodiments, the fiber component comprises beet pulp.

In some embodiments, the beet pulp is present in an amount of from about 0.5% to about 1.5% w/v. In some embodiments, the beet pulp is present in an amount of about 0.75% w/v. In other embodiments, the beet pulp is present in an amount of about 1.25% w/v. Yet other embodiments provide pet food compositions wherein the beet pulp is present in an amount of about 2% w/v.

In some embodiments, the fiber component comprises citrus pulp. In some embodiments, the citrus pulp is present in an amount of from about 0.875% to about 2.625% w/v. In some embodiments, the fiber component comprises citrus pulp. In some embodiments, the citrus pulp is present in an amount of from 0.1% to 2% w/v. In some embodiments, the citrus pulp is present in an amount of 1% w/v. In other embodiments, the citrus pulp is present in an amount of 2% w/v. In further embodiments, the citrus pulp is present in an amount of 2.625% w/v.

In some embodiments, the fiber component comprises a ratio of citrus pulp to beet pulp (citrus pulp:beet pulp) of from about 1.5:1 to about 2:1. In some embodiments, the fiber component comprises a ratio of citrus pulp to beet pulp (citrus pulp:beet pulp) of about 1.75:1.

In some embodiments, the *Camellia* extract is present in an amount of from about 0.043% to about 0.15% w/v. In some embodiments, the *Camellia* extract is present in an amount of 0.043% w/v. In some embodiments, the *Camellia* extract is present in an amount of 0.067% w/v. In some embodiments, the *Camellia* extract is present in an amount of 0.15% w/v. In some embodiments, the *Camellia* extract is of the type available from WellGen of North Brunswick, N.J.

In some embodiments, the *Camellia* extract and the fiber component are present in an amount effective to produce, after about 24 hours post-ingestion, a fecal lactic acid concentration of greater than about 1650 mg/L. In some embodiments, the *Camellia* extract and the fiber component are present in an amount effective to produce, after about 24 hours post-ingestion, a fecal lactic acid concentration of greater than about 1700 mg/L. In some embodiments, the *Camellia* extract and the fiber component are present in an amount effective to produce, after about 24 hours post-ingestion, a fecal lactic acid concentration of greater than about 1750 mg/L. In some embodiments, the *Camellia* extract and the fiber component are present in an amount effective to produce, after about 24 hours post-ingestion, a fecal lactic acid concentration of greater than about 1800 mg/L. In some embodiments, the *Camellia* extract and the fiber component are present in an amount effective to produce, after about 24 hours post-ingestion, a fecal lactic acid concentration of greater than about 1850 mg/L. In some embodiments, the *Camellia* extract and the fiber component are present in an amount effective to produce, after about 24 hours post-ingestion, a fecal lactic acid concentration of greater than about 1900 mg/L. In some embodiments, the *Camellia* extract and the fiber component are present in an amount effective to produce, after about 24 hours post-ingestion, a fecal lactic acid concentration of greater than about 1950 mg/L. In some embodiments, the *Camellia* extract and the fiber component are present in an amount effective to produce, after about 24 hours post-ingestion, a fecal lactic acid concentration of greater than about 2000 mg/L. In some embodiments, the *Camellia* extract and the fiber component are present in an amount effective to produce, after about 24 hours post-ingestion, a fecal lactic acid concentration of greater than about 2050 mg/L. In some embodiments, the *Camellia* extract and the fiber component are present in an amount effective to produce, after about 24 hours post-ingestion, a fecal lactic acid concentration of greater than about 2100 mg/L. In some embodiments, the *Camellia* extract and the fiber component are present in an amount effective to produce, after about 24 hours post-ingestion, a fecal lactic acid concentration of greater than about 2150 mg/L. In some embodiments, the *Camellia* extract and the fiber component are present in an amount effective to produce, after about 24 hours post-ingestion, a fecal lactic acid concentration of greater than about 2200 mg/L. In some embodiments, the *Camellia* extract and the fiber component are present in an amount effective to produce, after about 24 hours post-ingestion, a fecal lactic acid concentration of greater than about 2250 mg/L. In some embodiments, the *Camellia* extract and the fiber component are present in an amount effective to produce, after about 24 hours post-ingestion, a fecal lactic acid concentration of greater than about 2300 mg/L. In some embodiments, the *Camellia* extract and the fiber component are present in an amount effective to produce, after about 24 hours post-ingestion, a fecal lactic acid concentration of greater than about 2350 mg/L. In some embodiments, the *Camellia* extract and the fiber component are present in an amount effective to produce, after about 24 hours post-ingestion, a fecal lactic acid concentration of greater than about 2400 mg/L. In some embodiments, the *Camellia* extract and the fiber component are present in an amount effective to produce, after about 24 hours post-ingestion, a fecal lactic acid concentration of greater than about 2450 mg/L.

In other embodiments, the *Camellia* extract and the fermentable fiber component are present in an amount effective to produce, after about 24 hours post-ingestion, a fecal isovaleric acid concentration of less than about 30 mg/L. In further embodiments, the *Camellia* extract and the fermentable fiber component are present in an amount effective to produce, after about 24 hours post-ingestion, a fecal isovaleric acid concentration of less than about 25 mg/L. In other embodiments, the *Camellia* extract and the fermentable fiber component are present in an amount effective to produce, after about 24 hours post-ingestion, a fecal isovaleric acid concentration of less than about 20 mg/L. In other embodiments, the *Camellia* extract and the fermentable fiber component are present in an amount effective to produce, after about 24 hours post-ingestion, a fecal isovaleric acid concentration of less than about 15 mg/L. In other embodiments, the *Camellia* extract and the fermentable fiber component are present in an amount effective to produce, after about 24 hours post-ingestion, a fecal isovaleric acid concentration of less than about 10 mg/L. In other embodiments, the *Camellia* extract and the fermentable fiber component are present in an amount effective to produce, after about 24 hours post-ingestion, a fecal isovaleric acid concentration of less than about 5 mg/L.

In some embodiments, the *Camellia* extract comprises black tea, green tea, partially fermented tea (e.g. Oolong) or a combination thereof. In some embodiments, the *Camellia* extract comprises black tea.

In some embodiments, the total fiber concentration of the pet food composition is about 5% w/v.

Some embodiments of the present invention provide methods for treating, preventing, or ameliorating a symptom of a gastrointestinal disease, condition or disorder in a companion animal, comprising administering an effective amount of any one of the compositions described herein to a companion animal in need thereof. In some embodiments, the gastrointestinal disease, condition or disorder is selected from diarrhea; irritable bowel syndrome; ulcerative colitis and bowel distension.

Further embodiments of the present invention provide a methods for maintaining homeostatic balance of the intestinal ecosystem a companion animal, comprising administering an effective amount of the composition according to claim 1, to a companion animal in need thereof.

The pet food compositions set forth herein may be formed by extrusion to form a kibble-type pet food composition. In some embodiments, the milled raw ingredients of the composition are extruded and then a surface coating comprising a palatant and/or a nutritional oil is applied. In some embodiments, the kibble is spray coated in a tumbling mixer with a composition comprising a palatant and/or a nutritional oil. In other embodiments, the kibble is coated using a vacuum enrobing technique, wherein the kibble is subjected to vacuum and then exposed to coating materials after which the release of the vacuum drives the coating materials inside the kibble. Some embodiments provide methods of forming a pet food composition, comprising the steps of: extruding a mixture to form a kibble, the mixture comprising: a fiber component, and a *Camellia* extract obtained from the tissue of a tea which is greater than about 40% oxidized; and applying a surface coating to the kibble.

The pet food compositions described herein can include any additional ingredients which provide adequate nutrition for the animal. For example, a typical canine or feline diet for use in the present invention may contain from about 17 to about 50% crude protein (and preferably about 20 to about 40%), from about 8 to about 40% fat (and preferably about 12 to about 22%), and from about 0.5 to about 20% total dietary fiber (and preferably about 2 to about 10%), along with the multiple starch source, all percentages by weight. However, no specific ratios or percentages of these nutrients are required.

In some embodiments, the compositions described herein comprise from about 17 to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include beef, pork, lamb, equine, poultry, fish, and mixtures thereof.

In some embodiments, the compositions described herein comprise from about 8 to about 40% fat. Examples of suitable fats include animal fats and vegetable fats. Preferably the fat source is an animal fat source such as tallow or grease. Vegetable oils such as corn oil, sunflower oil, safflower oil, rape seed oil, soy bean oil, olive oil and other oils rich in monounsaturated and polyunsaturated fatty acids, may also be used.

In some embodiments, the compositions described herein comprise from about 10% to about 50% carbohydrate. Examples of suitable carbohydrates include grains or cereals such as rice, corn, millet, sorghum, alfalfa, barley, soybeans, canola, oats, wheat, rye, triticale and mixtures thereof. The compositions may also optionally comprise other materials such as dried whey and other dairy by-products.

The moisture content for the pet food compositions described herein can vary depending on the nature of the food composition. In some embodiments, the pet food compositions may be dry compositions (e.g., kibble), semi-moist compositions, wet compositions, or any mixture thereof. In some embodiments, the pet food composition is a complete and nutritionally balanced pet food. In some embodiments, the pet food may be a "wet food", "dry food", or food of "intermediate moisture" content.

As used herein, "wet food" describes a pet food that is typically sold in cans or foil bags and has a moisture content typically in the range of about 70% to about 90%.

As used herein, "dry food" describes a pet food that is of a similar composition to wet food but contains a limited moisture content typically in the range of about 5% to about 15% or 20% (typically in the form or small biscuit-like kibbles). In one preferred embodiment, the compositions have moisture content from about 5% to about 20%. Dry food products include a variety of foods of various moisture contents, such that they are relatively shelf-stable and resistant to microbial or fungal deterioration or contamination. In some embodiments, dry food compositions are extruded food products such as pet foods or snack foods for companion animals.

In some embodiments, the pet food compositions described herein may also comprise one or more fiber sources. As used herein, the term "fiber" includes all sources of "bulk" in the pet food composition, soluble or insoluble, fermentable or non-fermentable. In some embodiments, the fiber comprises a fiber from a plant source such as marine plants, but microbial sources of fiber may also be used.

In some embodiments, the ash content of the pet food composition ranges from less than 1% to about 15%, preferably from about 5% to about 10%.

In some embodiments, the pet food composition comprises from about 17% to about 50% protein, from about 8% to about 40% fat, from about 5% to about 10% ash content, and has a moisture content of about 5% to about 20%. In other embodiments, the pet food composition further comprises probiotics or prebiotics as described herein.

In some embodiments, the compositions described herein can be used as a dietary supplement and be co-administered with another pet food composition. The dietary supplement can have any suitable form such as a gravy, drinking water, beverage, yogurt, powder, granule, paste, suspension, chew, morsel, treat, snack, pellet, pill, capsule, tablet, sachet, or any other suitable delivery form. The dietary supplement can comprise the dietary formulations and optional compounds such as vitamins, preservatives, probiotics, prebiotics, and antioxidants. This permits the supplement to be administered to the animal in small amounts, or in the alternative, can be diluted before administration. In some embodiments, the dietary supplement may be admixed with a pet food composition or with water or other diluent prior to administration to the animal. When administered in a dietary supplement, the dietary formulations comprise from about 0.1 to about 90% of the supplement, preferably from about 3 to about 70%, more preferably from about 5 to about 60%.

In some embodiments, the compositions described herein are administered to an animal in the form of a nutraceutical composition. The nutraceutical composition comprises anyone of the pet food compositions described herein and one or more nutraceutically acceptable carriers, diluents, or excipients. Generally, nutraceutical compositions are prepared by admixing a compound or composition with excipients, buffers, binders, plasticizers, colorants, diluents, compressing agents, lubricants, flavorants, moistening agents, and the like, including other ingredients known to skilled artisans to be useful for producing nutraceuticals and formulating compositions that are suitable for administration to an animal as a nutraceutical. When administered in a nutraceutical composition, the dietary formulations comprise from about 0.1 to about 90% of the composition, preferably from about 3 to about 70%, more preferably from about 5 to about 60%.

The compositions described herein can be administered to the animal on an as-needed, on an as-desired basis, or on a regular basis.

According to the methods of the invention, administration of the dietary supplement, including administration as part of a dietary regimen, can span a period ranging from parturition through the adult life of the animal. In various embodiments, the animal is a companion animal such as a dog or cat. In certain embodiments, the animal is a young or growing animal. In some embodiments, the animal is an aging animal. In other embodiments administration begins, for example, on a regular or extended regular basis, when the animal has reached more than about 30%, 40%, or 50% of its projected or anticipated lifespan. In some embodiments, the animal has attained 40, 45, or 50% of its anticipated lifespan. In yet other embodiments, the animal is older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

In various embodiments, the compositions comprising the dietary formulations contain at least one of (1) one or more probiotics; (2) one or more inactivated probiotics; (3) one or more components of inactivated probiotics that promote health benefits similar to or the same as the probiotics, e.g., proteins, lipids, glycoproteins, and the like; (4) one or more prebiotics; and (5) combinations thereof. The probiotics or their components can be integrated into the compositions comprising the dietary formulations (e.g., uniformly or non-uniformly distributed in the compositions) or applied to the compositions comprising the dietary formulations (e.g., topically applied with or without a carrier). Such methods are known to skilled artisans, e.g., U.S. Pat. No. 5,968,569 and related patents.

Typical probiotics include, but are not limited to, probiotic strains selected from *Lactobacilli, Bifidobacteria*, or *Enterococci*, e.g., *Lactobacillus reuteri, Lactobacillus acidophilus, Lactobacillus animalis, Lactobacillus ruminis, Lactobacillus johnsonii, Lactobacillus casei, Lactobacillus paracasei, Lactobacillus rhamnosus, Lactobacillus fermentum*, and *Bifidobacterium* sp., *Enterococcus faecium* and *Enterococcus* sp. In some embodiments, the probiotic strain is selected from the group consisting of *Lactobacillus reuteri* (NCC2581; CNCM 1-2448), *Lactobacillus reuteri* (NCC2592; CNCM 1-2450), *Lactobacillus rhamnosus* (NCC2583; CNCM 1-2449), *Lactobacillus reuteri* (NCC2603; CNCM 1-2451), *Lactobacillus reuteri* (NCC2613; CNCM 1-2452), *Lactobacillus acidophilus* (NCC2628; CNCM 1-2453), *Bifidobacterium adolescentis* (e.g., NCC2627), *Bificlobacterium* sp. NCC2657 or *Enterococcus faecium* SF68 (NCIMB 10415).

In some embodiments, the compositions described herein may contain one or more prebiotics, e.g., fructo-oligosaccharides, gluco-oligosaccharides, galacto-oligosaccharides, isomalto-oligosaccharides, xylo-oligosaccharides, soybean oligosaccharides, lactosucrose, lactulose, and isomaltulose. In one embodiment, the prebiotic is chicory root, chicory root extract, insulin, or combinations thereof. Generally, prebiotics are administered in amounts sufficient to positively stimulate the healthy microflora in the gut and cause these "good" bacteria to reproduce.

The probiotics and prebiotics can be made part of the composition by any suitable means. Generally, the agents are mixed with the composition or applied to the surface of the composition, e.g., by sprinkling or spraying. In some embodiments, the pet food composition contains from about 0.1 to about 10% prebiotic. The prebiotics can be integrated into the compositions using methods known to skilled artisans.

In some embodiments, the prebiotic fiber component comprises beet pulp, citrus pulp, a cellulosic material or a mixture thereof. In other embodiments, the prebiotic fiber component comprises a mixture of beet pulp and citrus pulp.

In some embodiments, the pet food compositions further comprise from about 15% to about 50% protein. In other embodiments, the pet food compositions of the present invention comprise a source of hydrolyzed animal or plant protein. In some embodiments, the source of hydrolyzed animal or plant protein comprises chicken liver. In further embodiments, the source of hydrolyzed animal or plant protein is present in an active content of from about 25 to about 45 wt. %.

The invention will now be described in conjunction with the following, non-limiting examples.

EXAMPLES

Example 1

An exemplary pet food composition (Example 1) is prepared as set forth in Table 1 below. All amounts are provided in weight percent, based upon total weight of the pet food composition. The composition is formulated according to the nutrition standards set forth by the American Associated of Feed Control Officials (AAFCO) and the National Research Council (NRC). The composition may be produced by extrusion, dried, and then optionally coated with palatants.

TABLE 1

| Ingredient | Preferred Active Content Range (% w/v) |
|---|---|
| Citrus Pulp | 0.05-3 |
| Beet Pulp | 0.5-2 |
| Oxidized Camellia Extract | 0.05-0.25 |
| Corn, starch, common canning | 40-50 |
| Hydrolyzed Chicken Liver and Heart | 30-40 |
| Soybean oil, crude, degummed | 2-6 |
| Cellulose, Pelleted | 1-5 |
| Chicken, liver, digest, optimizor LDPE H | 1-5 |
| Lactic acid, food grade | 1-3 |
| Calcium carbonate | 1-3 |
| Dicalcium phosphate | 1-3 |
| Choice White Grease/Phos Acid | 0.1-2 |
| Flay Gen#1 + CWG | 0.1-2 |
| Glyceryl monostearate | 0.1-2 |
| Potassium chloride | 0.1-2 |
| Natural flavor, Pork, Liver, Digest, D'T | 0.1-2 |
| Sodium chloride, iodized | 0.1-2 |
| Choline chloride, liquid, 70% | 0.1-2 |

Example 2

Five (5) canines were randomly selected from a general population of beagles and mixed breed dogs. The canine subjects consisted of both neutered males and spayed females, who consumed varied, but typical, canine maintenance foods. The canines were selected to provide a varied compilation of feces that accurately represents the companion animal canine population at large; and would allow an objective assessment of the impact that a specific ingredient, or combination thereof, may have on a particular endpoint.

Example 3

Feces were collected from dogs fasted overnight into plastic bags containing oxygen absorbing packs to reduce oxygen tension and maintain viability of anaerobic microbiota. Pooled feces were homogenized in bacterial minimal media and separated of the largest particulates by centrifugation. After adding glycerol as a cryoprotectant the aliquots of viable bacteria were frozen and stored at (−) 80 C. Black tea and prebiotic fiber blends were sterilized via pasteurization prior to reconstitution in sterile water. Bacteria were incubated with prebiotic fiber as a carbon source as well as a published minimal media; methionine was added as a supplementary sulfur source. During (6 hours) and after (24 hours) of anaerobic incubation, production of lactic acid, pH in the colonic lumen (as observed in an in vitro colonic model), hydrogen sulfide ($H_2S$), and branched short chain fatty acids (BSCFA) were measured. The results of these experiments for nine (9) exemplary compositions of the present invention and eight (8) comparative examples are described in Table 2 and Table 3, respectively (below).

TABLE 2

Exemplary Compositions

| | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Ingredient | | | | | % w/v | | | | |
| Black Tea | 0.00045 | 0.0006 | 0.0006 | 0.00045 | 0.00045 | 0.0006 | 0.0003 | 0.0003 | 0.0003 |
| Beet Pulp | 0.00714 | 0.00714 | 0.00571 | 0.00571 | 0.00429 | 0.00429 | 0.00714 | 0.00571 | 0.00429 |
| Citrus Pulp | 0.0125 | 0.0125 | 0.01 | 0.01 | 0.0075 | 0.0075 | 0.0125 | 0.01 | 0.0075 |
| Yeast β-Glucan | — | — | 0.00286 | 0.00286 | 0.00571 | 0.00571 | — | 0.00286 | 0.00571 |
| Total Fiber | 0.01 | 0.01 | 0.01 | 0.01 | 0.01 | 0.01 | 0.01 | 0.01 | 0.01 |
| Parameter Evaluations at 24 hours ($t_{24}$) | | | | | | | | | |
| Lactic acid | 2470.77 | 2526.82 | 1867.52 | 2200.74 | 1772.55 | 1917.15 | 2372.39 | 1986.31 | 1657.50 |
| pH | 4.57 | 4.53 | 4.81 | 4.56 | 4.92 | 4.80 | 4.60 | 4.77 | 4.89 |
| Gas | 1.45 | 0.50 | 1.55 | 0.85 | 1.00 | 2.05 | 2.10 | 1.9 | 1.75 |
| Hydrogen sulfide | 230 | 180 | 280 | 180 | 170 | 59 | 345 | 365 | 415 |
| Isovaleric acid | — | — | — | — | — | — | 14.54 | 14.70 | 27.07 |

TABLE 3

Comparative Examples

| | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
|---|---|---|---|---|---|---|---|---|
| Ingredient | | | | | % w/v | | | |
| Black Tea | 0.0006 | 0.00045 | 0.00015 | 0.00015 | 0.00015 | 0.0003 | 0.00015 | — |
| Beet Pulp | 0.00286 | 0.00286 | 0.00714 | 0.00571 | 0.00286 | 0.00286 | 0.00429 | — |
| Citrus Pulp | 0.005 | 0.005 | 0.0125 | 0.01 | 0.005 | 0.005 | 0.0075 | — |
| Yeast β-Glucan | 0.00857 | 0.00857 | — | 0.00286 | 0.00857 | 0.00857 | 0.00571 | — |
| Total Fiber | 0.01 | 0.01 | 0.01 | 0.01 | 0.01 | 0.01 | 0.01 | 0.01 |
| Parameter Evaluations at 24 hours ($t_{24}$) | | | | | | | | |
| Lactic acid | 766.26 | 1181.27 | 2261.30 | 1832.60 | 1469.17 | 1090.23 | 1548.90 | 269.56 |
| pH | 5.35 | 5.13 | 4.76 | 4.93 | 5.10 | 5.60 | 5.13 | 6.56 |
| Gas | 2.30 | 0.80 | 2.75 | 2.80 | 2.70 | 2.25 | 2.40 | 1.60 |
| Hydrogen sulfide | 127 | 270 | 475 | 510 | 495 | 620 | 515 | 370 |
| Isovaleric acid | — | 6.11 | 31.30 | 42.13 | 42.74 | 49.04 | 49.31 | 104.61 |

As illustrated by the data reported in Table 2 (above), lactic acid was increased at 24 hours ($t_{24}$) post incubation (correlates with post-ingestion), in a manner dependent on the concentration of a *Camellia* extract obtained from the tissue of a tea which is greater than about 40% oxidized and prebiotic fiber. The results also describe a decrease in volumetric gas production resulting from administration of exemplary compositions of the present invention, which correlates with decreased post-prandial gastrointestinal distress and flatulence.

The multi-faceted benefits provided by compositions of the present invention are also underscored by their ability to decrease hydrogen sulfide production by gut bacteria. Hydrogen sulfide is an odiferous and noxious gaseous molecule produced by commensal gut bacteria and decidedly off-putting to those tasked with sanitation of excrement. Additionally, hydrogen sulfide is implicated in inflammatory processes.

Volatile BSCFAs (e.g. isovaleric acid) are generated by commensal gut microbe putrefaction of unabsorbed dietary proteins. Although not necessarily detrimental per se, these protein putrefaction products are indicative of the production of uremic toxins implicated in etiological progression of chronic renal failure. As shown in Table 2 (above), exemplary compositions of the present invention decrease protein putrefaction to a sufficient extent, as evidenced by decreased production of isovaleric acid by commensal gut bacteria.

As such, these results demonstrate that a *Camellia* extract obtained from the tissue of a tea which is greater than about 40% oxidized unexpectedly enhances the capacity of certain fiber sources to stimulate lactate production by commensal gut microbiota. And, the addition of certain concentrations of the aforementioned *Camellia* extract decreases the negative consequences of excess fermentation capacity, including: gas and hydrogen sulfide production as well as protein putrefaction. Most importantly, and as the data demonstrates, the benefits provided by the inventive compositions of the present invention are non-linear and truly unexpected.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A pet food composition comprising:
   a *Camellia* extract obtained from the tissue of a tea which is greater than about 40% oxidized; and
   a fiber component,
   wherein the *Camellia* extract and the fiber component are present in an amount effective to provide, after about 24 hours post-ingestion, a fecal hydrogen sulfide concentration of less than 450 mg/L, and a colonic lumen pH of less than 5.0, and
   wherein the *Camellia* extract is present in an amount of from 0.067% to 0.15% w/v.

2. The pet food composition according to claim 1, wherein the fiber component comprises a fiber type selected from: a hemicellulose; a cellulose; pectin; an oligosaccharide of xylose, galactose or fructose; a resistant starch, and a combination of two or more thereof.

3. The pet food composition according to claim 2, wherein the fiber component comprises a soluble fiber source selected from: oats; apple; sugar cane; citrus pulp; beet pulp; grains, or a combination of two or more thereof.

4. The pet food composition according to claim 1, wherein the fiber component comprises beet pulp.

5. The pet food composition according to claim 4, wherein the beet pulp is present in an amount of from about 0.5% to about 1.5% w/v.

6. The pet food composition according to claim 4, wherein the fiber component further comprises citrus pulp.

7. The pet food composition according to claim 6, wherein the fiber component comprises a ratio of citrus pulp to beet pulp (citrus pulp:beet pulp) of from about 1.5:1 to about 2:1.

8. The pet food composition according to claim 4, wherein the fiber component comprises a ratio of citrus pulp to beet pulp of about 1.75:1.

9. The pet food composition according to claim 1, wherein the fiber component comprises citrus pulp in an amount of from 0.875% to 2.625% w/v.

10. The pet food composition according to claim 1, wherein the *Camellia* extract and the fiber component are present in an amount effective to produce, after about 24 hours post-ingestion, a fecal lactic acid concentration of greater than about 1650 mg/L.

11. The pet food composition according to claim 1, wherein the *Camellia* extract and the fermentable fiber component are present in an amount effective to produce, after about 24 hours post-ingestion, a fecal isovaleric acid concentration of less than about 30 mg/L.

12. The pet food composition according to claim 1, wherein the *Camellia* extract comprises black tea.

13. The pet food composition according to claim 1, wherein the total fiber concentration is about 5% w/v.

14. The pet food composition according to claim 1, having a moisture content of from about 5% to about 20% w/v.

15. The pet food composition according to claim 1, further comprising a source of hydrolyzed animal or plant protein.

16. The pet food composition according to claim 15, wherein the source of hydrolyzed animal or plant protein comprises chicken liver.

17. A method for treating, preventing, or ameliorating a symptom of a gastrointestinal disease, condition or disorder in a companion animal, comprising administering an effective amount of the composition according to claim 1, to a companion animal in need thereof.

18. A method for maintaining homeostatic balance of the intestinal ecosystem of a companion animal, comprising administering an effective amount of the composition according to claim 1, to a companion animal in need thereof.

19. A pet food composition comprising:
   a *Camellia* extract obtained from the tissue of a tea which is greater than about 40% oxidized; and
   a fiber component,
   wherein the fiber component comprises beet pulp,
   wherein the beet pulp is present in an amount of from about 0.5% to about 1.5% w/v,
   wherein the *Camellia* extract and the fiber component are present in an amount effective to provide, after about 24 hours post-ingestion, a fecal hydrogen sulfide concentration of less than 450 mg/L, and a colonic lumen pH of less than 5.0, and
   wherein the *Camellia* extract is present in an amount of from 0.067% to 0.15% w/v.

20. A pet food composition comprising:
   a *Camellia* extract obtained from the tissue of a tea which is greater than about 40% oxidized; and
   a fiber component,
   wherein the fiber component comprises citrus pulp in an amount of from 0.875% to 2.625% w/v, and
   wherein the *Camellia* extract and the fiber component are present in an amount effective to provide, after about 24 hours post-ingestion, a fecal hydrogen sulfide concentration of less than 450 mg/L, and a colonic lumen pH of less than 5.0, and
   wherein the *Camellia* extract is present in an amount of from 0.067% to 0.15% w/v.

* * * * *

UNITED STATES PATENT AND TRADEMARK OFFICE
CERTIFICATE OF CORRECTION

PATENT NO.       : 11,260,099 B2
APPLICATION NO.  : 15/381835
DATED            : March 1, 2022
INVENTOR(S)      : Matthew Jackson et al.

It is certified that error appears in the above-identified patent and that said Letters Patent is hereby corrected as shown below:

On the Title Page

Item (56) under "U.S. PATENT DOCUMENTS", Line 3, delete "Sunvoid" and insert -- Sunvold --, therefor.

Signed and Sealed this
Seventeenth Day of May, 2022

Katherine Kelly Vidal
*Director of the United States Patent and Trademark Office*